United States Patent
Morré

(10) Patent No.: US 8,465,939 B2
(45) Date of Patent: Jun. 18, 2013

(54) AGING-RELATED CIRCULATING PARTICLE-ASSOCIATED LIPOPROTEIN B OXIDASE (APOBNOX) AND INHIBITORS THEREOF

(75) Inventor: D. James Morré, West Lafayette, IN (US)

(73) Assignee: Nox Technologies, Inc., west Lafayette, IN (US)

( * ) Notice: Subject to any disclaimer, the term of this patent is extended or adjusted under 35 U.S.C. 154(b) by 0 days.

(21) Appl. No.: 13/039,170

(22) Filed: Mar. 2, 2011

(65) Prior Publication Data

US 2011/0217401 A1 Sep. 8, 2011

Related U.S. Application Data

(60) Provisional application No. 61/309,687, filed on Mar. 2, 2010.

(51) Int. Cl.
*G01N 33/53* (2006.01)
*C12Q 1/00* (2006.01)
*C12N 9/00* (2006.01)

(52) U.S. Cl.
USPC .................................. 435/7.7; 435/4; 435/183

(58) Field of Classification Search
None
See application file for complete search history.

(56) References Cited

U.S. PATENT DOCUMENTS

| | | | |
|---|---|---|---|
| 6,361,807 B1 * | 3/2002 | Aviram et al. | 424/744 |
| 6,416,808 B1 | 7/2002 | Crea | |
| 6,849,770 B2 | 2/2005 | Guzman et al. | |
| 6,878,514 B1 | 4/2005 | Morré et al. | |
| 6,906,100 B2 | 6/2005 | Fotinos et al. | |
| 7,053,188 B2 | 5/2006 | Morré et al. | |
| 7,098,246 B2 | 8/2006 | Geelings et al. | |
| 7,416,748 B2 | 8/2008 | Olalde Rangel | |
| 7,713,569 B2 | 5/2010 | Crea | |
| 7,776,563 B2 | 8/2010 | Hazen et al. | |
| 2002/0054924 A1 * | 5/2002 | Leahy et al. | 424/732 |
| 2003/0064970 A1 | 4/2003 | Grainger et al. | |
| 2003/0225160 A1 | 12/2003 | Geerlings et al. | |
| 2003/0236202 A1 | 12/2003 | Geelings et al. | |
| 2004/0001817 A1 | 1/2004 | Giampapa | |
| 2004/0132821 A1 | 7/2004 | Crea | |
| 2007/0122505 A1 | 5/2007 | Elgaard et al. | |
| 2007/0224287 A1 | 9/2007 | Wright et al. | |
| 2008/0160042 A1 | 7/2008 | Olalde Rangel | |
| 2008/0262081 A1 | 10/2008 | Raederstorff et al. | |
| 2009/0004334 A1 | 1/2009 | Nair | |
| 2009/0068292 A1 | 3/2009 | Jiang et al. | |
| 2009/0181413 A1 | 7/2009 | Itoh et al. | |
| 2010/0016299 A1 | 1/2010 | Griebenow et al. | |
| 2010/0022464 A1 | 1/2010 | Benavente-Garcia | |
| 2010/0130621 A1 | 5/2010 | Raederstorff et al. | |

FOREIGN PATENT DOCUMENTS

| | | |
|---|---|---|
| WO | 2004/044011 | 5/2004 |
| WO | 2009/049900 | 4/2009 |
| WO | 2009/055840 | 5/2009 |
| WO | 2010/010320 | 1/2010 |
| WO | 2011/022387 | 2/2011 |

OTHER PUBLICATIONS

International Search Report and Written Opinion, mailed May 26, 2011, in corresponding International Application No. PCT/US11/26877, filed Mar. 2, 2011, 14 pp.
NCBI Nucleotide Accession No. U81006.1, Dec. 19, 1996, "Human p76 mRNA, complete cds", 4pp.
"The health benefits of Hydroxytyrosol and Tyrosol," http://www.zhion.com/phytonutrients/Hydroxytyrosol.html, downloaded Feb. 7, 2011, 2 pp.
"Hydroxytyrosol," http://en.wikipedia.org/wiki/Hydroxytyrosol, downloaded Feb. 7, 2011, 2 pp.
"Phytochemicals," http://www.phytochemicals.info/phytochernicals/hydroxytyrosol.php, downloaded Feb. 7, 2011, 1 pp.
"Tyrosol," http://en.wikipedia.org/wiki/Tyrosol, downloaded Feb. 4, 2011, 1 pp.
Acin et al. (2006) "Hydroxytyrosol Administration Enhances Atherosclerotic Lesion Development in Apo E Deficient Mice," J. Biochem. 140:383-391.
Bjelakovic et al. (Feb. 28, 2007) "Mortality in Randomized Trials of Antioxidant Supplements for Primary and Secondary Prevention," JAMA 297(8):842-857. Also, Data errors (Feb. 20, 2008) 299(7):765-766.
Butler et al. (1982) "Kinetics and Mechanism of the Reduction of Ferricytochrome *c* by the Superoxide Anion," J. Biol. Chem. 257(18):10747-10750.

(Continued)

*Primary Examiner* — Chris R Tate
*Assistant Examiner* — Douglas F White
(74) *Attorney, Agent, or Firm* — Dorsey & Whitney LLP

(57) ABSTRACT

Provided is an age-related apolipoprotein B oxidase (apoBNOX) found tightly associated with the low-density lipoprotein particles and believed to be responsible for oxidizing lipoprotein particles and initiating atherogenesis. It causes damage by directly oxidizing the apolipoprotein B protein and indirectly oxidizing the lipids in the particles due to superoxide formation by the apoBNOX and its conversion into hydrogen peroxide. apoBNOX activity is inhibited by tyrosol and hydroxytyrosol and components of white wine, important components of French and Mediterranean diets, which seem to be a very good source of inhibitors of the apolipoprotein B oxidase. Agents comprising at least one naturally-occurring apoBNOX inhibitor and compositions lessen, ameliorate or treat disorders and complications resulting from cell damage caused by oxidation of apolipoprotein B. Also provided is an assay system comprising recombinant apoBNOX or an equivalent peptide and apolipoprotein B purified from human sera as a model to screen for agents and supplements that lower apoBNOX activity when administered orally.

8 Claims, 7 Drawing Sheets

OTHER PUBLICATIONS

Castilla et al. (2008) "Comparative effects of dietary supplementation with red grape juice and vitamin E on production of superoxide by circulating neutrophil NADPH oxidase in hemodialysis patients," Am J Clin Nutr 87:1053-1061.

Giovannini et al. (1999) "Tyrosol, the Major Olive Oil Biophenol, Protects Against Oxidized-LDL-Induced Injury in Caco-2 Cells," The Journal of Nutrition 129:1269-1277.

Gonzalez-Santiago, et al. (2006) "One-month administration of hydroxytyrosol, a phenolic antioxidant present in olive oil, to hyperlipemic rabbits improves blood lipid profile, antioxidant status and reduces atherosclerosis development," Atherosclerosis 188:35-42.

Holvoet, P. (1999) "Endothelial Dysfunction, Oxidation of Low-Density Lipoprotein, and Cardiovascular Disease," Ther. Apher. 3(4):287-293, Blackwell Science, Inc.

Hostetler et al. (2009) "Cancer Site-Specific Isoforms of ENOX2 (tNOX), A Cancer-Specific Cell Surface Oxidase," Clin. Proteom. 5:46-51, published online Sep. 4, 2008.

Jiang et al. (2008) "Molecular Cloning and Characterization of a Candidate Human Growth-Related and Time-Keeping Constitutive Cell Surface Hydroquinone (NADH) Oxidase," Biochemistry 47:14028-14038.

Lucas et al. (2010) "Surface-Active Properties of Lipophilic Antioxidants Tyrosol and Hydroxytyrosol Fatty Acid Esters: A Potential Explanation for the Nonlinear Hypothesis of the Antioxidant Activity in Oil-in-Water Emulsions," J. Agric. Food Chem. 58(13):8021-8026, published online Jun. 4, 2010.

Mayo et al. (1990) "Kinetic Microplate Assay for Superoxide Production by Neutrophils and Other Phagocytic Cells," Meth. Enzyme. 186:567-575.

Miro-Casas et al. (2003) "Hydroxytyrosol Disposition in Humans," Clinical Chemistry 49(6):945-952.

Miro-Casas et al. (2003) "Tyrosol and hydroxytyrosol are absorbed from moderate and sustained doses of virgin olive oil in humans," European Journal of Clinical Nutrition 57:186-190.

Morré, D.J. (1998) "NADH Oxidase: A Multifunctional Ectoprotein of the Eukaryotic Cell Surface," Plasma Membrane Redox Systems and Their Role in Biological Stress and Disease (Asard, H., Bérczi, A. and Caubergs, R.J., Eds) pp. 121-156, Kluwer Academic Publishers, Dordrecht, Netherlands.

Morré et al. (2003) "Cell Surface NADH Oxidases (ECTO-NOX Proteins) With Roles in Cancer, Cellular Time-Keeping, Growth, Aging and Neurodegenerative Diseases" Free Radical Res. 37(8):795-808.

Morré et al. (2000) "Surface oxidase and Oxidative Stress Propagation in Aging," J. Exp. Biol. 203:1513-1521.

Morré et al. (2003) "An aging-related cell surface Nadh oxidase (arNOX) generates superoxide and is inhibited by coenzyme Q," Mol Cell. Biochem. 254:101-109.

Morré et al. (2006) "Aging-Related Cell Surface ECTO-NOX Protein, arNOX, a Preventive Target to Reduce Atherogenic Risk in the Elderly," Rejuvenation Research 9(2):231-236.

Morré et al. (2008) "Supplementation with $CoQ_{10}$ lowers age-related (ar) NOX levels in healthy subjects," BioFactors 32:221-230.

Morré et al. (2008) "arNOX activity of saliva as a non-invasive measure of coenzyme $Q_{10}$ response in human trials," BioFactors 32:231-235.

Oliveras-Lopez et al. (2008) "An Extra-Virgin Olive Oil Rich in Polyphenolic Compounds Has Antioxidant Effects in Of1 Mice," The Journal of Nutrition 138:1074-1078.

Rietjens et al. (2007) "The olive oil antioxidant hydroxytyrosol efficiently protects against the oxidative stress-induced impairment of the NO response of isolated rat aorta," Am J. Physiol Heart Circ Physiol 292:H1931-H1936.

Samuel et al. (Oct. 22, 2008) "Akt/FOXO3a/SIRT1 Mediated Cardioprotection by n-Tyrosol against Ischemic Stress in Rat in vivo model of Myocardial Infarction: Switching Gears towards Survival and Longevity," J. Agric Food Chem. 56(20):9692-9698.

Schmuck et al. (1995) "Effect of Aging on Susceptibility of Low-Density Lipoproteins to Oxidation," Clin. Chem. 41(11):1628-1632.

Weaver et al. (Aug. 1, 2009) "Research Highlights from the Purdue-UAB Botanics Research Center for Age Related Diseases," Pharm Biol. 47(8):768-773.

Yazdanparast et al. (2008) "Comparative effects of *Artemisia dracunculus*, *Satureja hortensis* and *Origanum majorana* on inhibition of blood platelet adhesion, aggregation and secretion," Vascular Pharmacology 48:32-37.

* cited by examiner

```
  1 MGAPLPVLSP PRWPPLLLLS LLLLGAVPGP PPSGAFYLPG LAPVNFCDSE KKSDECKAEI
 61 ELFVNPLGSV ESVLPYEYTA FDFQQASEGS RPGENLGQPL FGERIEFSPI KFFNKKETQ
121 FLCCTKTYHI SKAEDKQPLE FLKKSMLLNY QRWIVINMP VTWCYDVEDG QRFCNIGFPI
181 GCYIPDKGHA MDACVISSDF HKRDTFYIFN HVDIKILYRV VETGSKGAPL VAASLEPKSF
241 KHHIOKPDC

Conserved C6/C8
Adenine nucleotide binding site GXXXG at amino acids 97-102
Putative protein disulfide interchange site CXXXC
Putative copper sites YQH and STH
Twenty five amino acid sequence having 56% sequence summary with the LDL
receptor putative binding surface
```

Figure 5

SEQUENCE LISTING

<160> NUMBER OF SEQ ID NOS: 3

<210> SEQ ID NO 1
<211> LENGTH: 2391
<212> TYPE: DNA
<213> ORGANISM: Homo sapiens

<400> SEQUENCE: 1

```
cgcaaccgga actagccttc tgggggccgg cttggtttat ctctggcggc cttgtagtcg      60
tctccgagac tccccacccc tccttccctc ttgaccccct aggtttgatt gcccttcc      120 cgaaacaact atcatgagcg cgaggctgcc ggtgttgtct ccacctcggt ggccgcggct     180
gttgctgctg tcgctgctcc tgctggggc ggttcctggc ccgcgccgga gcggcgcttt     240
ctacctgccc ggcctggcgc ccgtcaactt ctgcgacgaa gaaaaaaaga gcgacgagtg     300
caaggccgaa atagaactat ttgtgaacag acttgattca gtggaatcag ttcttcctta    360
tgaatacaca gcgtttgatt tttgccaagc atcagaagga aagcgcccat ctgaaaatct    420
tggtcaggta ctattcgggg aaagaattga accttcacca tataagttta cgtttaataa    480
gaaggagacc tgtaagcttg tttgtacaaa aacataccat acagagaaag ctgaagacaa    540
acaaaagtta gaattcttga aaaaaagcat gttattgaat tatcaacatc actggattgt    600
ggataatatg cctgtaacgt ggtgttacga tgttgaagat ggtcagaggt tctgtaatcc    660
tggatttcct attggctgtt acattacaga taaaggccat gcaaaagatg cctgtgttat    720 tagttcgat ttccatgaaa gagatacatt ttacatcttc aaccatgttg acatcaaaat    780
atactatcat gttgttgaaa ctgggtccat gggagcaaga ttagtggctg ctaaacttga    840
accgaaaagc ttcaaacata cccatataga taaaccagac tgctcagggc ccccatgga    900 cataagtaac aaggcttctg gggagataaa aattgcctat acttactctg ttagcttcga    960
```

```
ggaagatgat aagatcagat gggcgtctag atgggactat attctggagt ctatgcctca    1020
tacccacatt cagtggttta gcattatgaa ttccctggtc attgttctct tcttatctgg    1080
aatggtagct atgattatgt tacggacact gcacaaagat attgctagat ataatcagat    1140
ggactctacg gaagatgccc aggaagaatt tggctggaaa cttgttcatg gtgatatatt    1200
ccgtcctcca agaaaaggga tgctgctatc agtctttcta ggatccggga cacagatttt    1260
aattatgacc tttgtgactc tattttcgc ttgcctggga tttttgtcac ctgccaaccg     1320
aggagcgctg atgacgtgtg ctgtggtcct gtgggtgctg ctgggcaccc ctgcaggcta    1380
tgttgctgcc agattctata agtcctttgg aggtgagaag tggaaaacaa atgttttatt    1440
aacatcattt ctttgtcctg ggattgtatt tgctgacttc tttataatga atctgatcct    1500
ctggggagaa ggatcttcag cagctattcc ttttgggaca ctggttgcca tattggccct    1560
ttggttctgc atatctgtgc ctctgacgtt tattggtgca actttggtt ttaagaagaa     1620 tgccattgaa cacccagttc gaaccaatca gattccacgt cagattcctg aacagtcgtt    1680
ctacacgaag cccttgcctg gtattatcat gggagggatt ttgcccttg gctgcatctt     1740 tatacaactt ttcttcattc tgaatagtat ttggtcacac cagatgtatt acatgtttgg    1800 cttcctatttt ctggtgttta tcattttggt tattacctgt tctgaagcaa ctatacttct   1860
ttgctatttc cacctatgtg cagaggatta tcattggcaa tggcgttcat tccttacgag    1920
tggctttact gcagtttatt tcttaatcta tgcagtacac tacttctttt caaaactgca    1980
gatcacggga acagcaagca caattctgta ctttggttat accatgataa tggttttgat    2040 cttcttttctt tttacaggaa caattggctt ctttgcatgc ttttggtttg ttaccaaaat   2100
atacagtgtg gtgaaggttg actgaagaag tccagtgtgt ccagttaaaa cagaaataaa    2160
ttaaactctt catcaacaaa gacctgtttt tgtgactgcc ttgagtttta tcagaattat    2220
tggcctagta atccttcaga aacaccgtaa ttctaaataa acctcttccc atacacctttt   2280 cccccataag atctgtcttc aacactataa agcatttgta ttgtgatttg attaagtata    2340
tatttggttg ttctcaatga agagcaaatt taaatattat gtgcatttga a            2391
```

<210> SEQ ID NO 2
<211> LENGTH: 663
<212> TYPE: PRT
<213> ORGANISM: Homo sapiens

<400> SEQUENCE: 2

```
Met Ser Ala Arg Leu Pro Val Leu Ser Pro Pro Arg Trp Pro Arg Leu
1               5                   10                  15

Leu Leu Leu Ser Leu Leu Leu Leu Gly Ala Val Pro Gly Pro Arg Arg
                20                  25                  30

Ser Gly Ala Phe Tyr Leu Pro Gly Leu Ala Pro Val Asn Phe Cys Asp
            35                  40                  45

Glu Glu Lys Lys Ser Asp Glu Cys Lys Ala Glu Ile Glu Leu Phe Val
        50                  55                  60

Asn Arg Leu Asp Ser Val Glu Ser Val Leu Pro Tyr Glu Tyr Thr Ala
65                  70                  75                  80

Phe Asp Phe Cys Gln Ala Ser Glu Gly Lys Arg Pro Ser Glu Asn Leu
                85                  90                  95

Gly Gln Val Leu Phe Gly Glu Arg Ile Glu Pro Ser Pro Tyr Lys Phe
            100                 105                 110

Thr Phe Asn Lys Lys Glu Thr Cys Lys Leu Val Cys Thr Lys Thr Tyr
        115                 120                 125
```

```
His Thr Glu Lys Ala Glu Asp Lys Gln Lys Leu Glu Phe Leu Lys Lys
    130                 135                 140

Ser Met Leu Leu Asn Tyr Gln His His Trp Ile Val Asp Asn Met Pro
145                 150                 155                 160

Val Thr Trp Cys Tyr Asp Val Glu Asp Gly Gln Arg Phe Cys Asn Pro
                165                 170                 175

Gly Phe Pro Ile Gly Cys Tyr Ile Thr Asp Lys Gly His Ala Lys Asp
            180                 185                 190

Ala Cys Val Ile Ser Ser Asp Phe His Glu Arg Asp Thr Phe Tyr Ile
        195                 200                 205

Phe Asn His Val Asp Ile Lys Ile Tyr Tyr His Val Val Glu Thr Gly
    210                 215                 220

Ser Met Gly Ala Arg Leu Val Ala Ala Lys Leu Glu Pro Lys Ser Phe
225                 230                 235                 240

Lys His Thr His Ile Asp Lys Pro Asp Cys Ser Gly Pro Pro Met Asp
                245                 250                 255

Ile Ser Asn Lys Ala Ser Gly Glu Ile Lys Ile Ala Tyr Thr Tyr Ser
            260                 265                 270

Val Ser Phe Glu Glu Asp Asp Lys Ile Arg Trp Ala Ser Arg Trp Asp
        275                 280                 285

Tyr Ile Leu Glu Ser Met Pro His Thr His Ile Gln Trp Phe Ser Ile
    290                 295                 300

Met Asn Ser Leu Val Ile Val Leu Phe Leu Ser Gly Met Val Ala Met
305                 310                 315                 320

Ile Met Leu Arg Thr Leu His Lys Asp Ile Ala Arg Tyr Asn Gln Met
                325                 330                 335

Asp Ser Thr Glu Asp Ala Gln Glu Glu Phe Gly Trp Lys Leu Val His
            340                 345                 350

Gly Asp Ile Phe Arg Pro Pro Arg Lys Gly Met Leu Leu Ser Val Phe
        355                 360                 365

Leu Gly Ser Gly Thr Gln Ile Leu Ile Met Thr Phe Val Thr Leu Phe
    370                 375                 380

Phe Ala Cys Leu Gly Phe Leu Ser Pro Ala Asn Arg Gly Ala Leu Met
385                 390                 395                 400

Thr Cys Ala Val Val Leu Trp Val Leu Leu Gly Thr Pro Ala Gly Tyr
                405                 410                 415

Val Ala Ala Arg Phe Tyr Lys Ser Phe Gly Gly Glu Lys Trp Lys Thr
            420                 425                 430

Asn Val Leu Leu Thr Ser Phe Leu Cys Pro Gly Ile Val Phe Ala Asp
        435                 440                 445

Phe Phe Ile Met Asn Leu Ile Leu Trp Gly Glu Gly Ser Ser Ala Ala
    450                 455                 460

Ile Pro Phe Gly Thr Leu Val Ala Ile Leu Ala Leu Trp Phe Cys Ile
465                 470                 475                 480

Ser Val Pro Leu Thr Phe Ile Gly Ala Tyr Phe Gly Phe Lys Lys Asn
                485                 490                 495

Ala Ile Glu His Pro Val Arg Thr Asn Gln Ile Pro Arg Gln Ile Pro
            500                 505                 510

Glu Gln Ser Phe Tyr Thr Lys Pro Leu Pro Gly Ile Ile Met Gly Gly
        515                 520                 525

Ile Leu Pro Phe Gly Cys Ile Phe Ile Gln Leu Phe Phe Ile Leu Asn
    530                 535                 540

Ser Ile Trp Ser His Gln Met Tyr Tyr Met Phe Gly Phe Leu Phe Leu
545                 550                 555                 560
```

```
Val Phe Ile Ile Leu Val Ile Thr Cys Ser Glu Ala Thr Ile Leu Leu
                565                 570                 575

Cys Tyr Phe His Leu Cys Ala Glu Asp Tyr His Trp Gln Trp Arg Ser
                580                 585                 590

Phe Leu Thr Ser Gly Phe Thr Ala Val Tyr Phe Leu Ile Tyr Ala Val
            595                 600                 605

His Tyr Phe Phe Ser Lys Leu Gln Ile Thr Gly Thr Ala Ser Thr Ile
        610                 615                 620

Leu Tyr Phe Gly Tyr Thr Met Ile Met Val Leu Ile Glu Phe Leu Phe
625                 630                 635                 640

Thr Gly Thr Ile Gly Phe Phe Ala Cys Phe Trp Phe Val Thr Lys Ile
                645                 650                 655

Tyr Ser Val Val Lys Val Asp
                660

<210> SEQ ID NO 3
<211> LENGTH: 27
<212> TYPE: PRT
<213> ORGANISM: Artificial Sequence
<220> FEATURE:
<223> OTHER INFORMATION: Synthetic construct:  peptide equivalent of
      apolipoprotein B for apoBNOX inhibitor assays

<400> SEQUENCE: 3

Phe His Cys Arg Asp Gly Asn Cys Ile His Asn His Trp Gln Cys Asp
1               5                   10                  15

Gly Asp Tyr Asp Cys Gly Glu Gly Ser Asp Glu
                20                  25
```

AGING-RELATED CIRCULATING PARTICLE-ASSOCIATED LIPOPROTEIN B OXIDASE (APOBNOX) AND INHIBITORS THEREOF

CROSS-REFERENCE TO RELATED APPLICATIONS

This application claims benefit of U.S. Provisional Application No. 61/309,687, filed Mar. 2, 2010, which application is incorporated by reference herein to the extent there is no inconsistency with the present disclosure.

REFERENCE TO SEQUENCE LISTING

The Sequence Listing submitted herewith is incorporated by reference herein.

BACKGROUND

The field of this disclosure relates to aging-associated oxidative damage, and specifically, to an aging-specific particle associated Lipoprotein B NADH oxidase (apoBNOX) attached to circulating lipoprotein particles, its use as a target to identify agents for the prevention or treatment of disorders caused by oxidative damage to circulating lipoproteins and the identification of such agents for use as dietary supplements and/or pharmaceutical preparations with examples derived from olive oil and white wine, including tyrosol (4-hydroxyphenethyl alcohol) and its hydroxylated derivative, hydroxytyrosol.

apoBNOX is a member of the ECTO-NOX or ENOX family of proteins. These proteins exhibit one or more cyanide-resistant external plasma membrane or soluble hydroquinone oxidases capable of catalyzing protein disulfide interchange and that oxidize NAD(P)H as an alternate substrate (NADH oxidase=NOX) (Morré, 1998, in Plasma Membrane Redox Systems and Their Role in Biological Stress and Disease, H. Asard, A. Bérczi and R. J. Caubergs, eds., pp. 121-156, Kluwer Academic Publishers, Dordrecht, Netherlands; Morré and Morré, 2003, Free Radical Res. 37: 795-808). Based on activity characteristics, at least three but distinct ECTO-NOX or ENOX (for external cell surface NOX) proteins have been described. These proteins are characterized by the property of having two distinct biochemical activities, hydroquinone (NAD(P)H) oxidation and protein disulfide-thiol interchange, that alternate. One (CNOX or ENOX1) is constitutive with an activity that is widely distributed among animals, plants and yeasts (Jiang et al., 2008, Biochemistry 48: 14018-14038). A second ENOX activity is tumor or cancer-associated, designated tNOX or ENOX2 (Hostetler et al., 2009, Clin. Proteomics 5: 46-51). ENOX 2 proteins are inhibited by a series of quinone site inhibitors all with anticancer activity. A third protein with ENOX-like activity (designated arNOX) is age-related (Morré et al., 2003, Mol. Cell. Biochem. 254: 101-109) and predominant only on cell surfaces and body fluids of aged individuals and on plasma membrane of late passage cultured cells or senescent plant parts. Shed forms of both activities are found in body fluids and in culture media conditioned by the growth of mammalian or plant cells. arNOX differs from ENOX1 and ENOX2 by generating superoxide based on superoxide susceptible oxidation of ferricytochrome c, a standard method for measurement of superoxide generation (Butler et al., 1982, J. Biol. Chem. 257: 10747-10750).

apoBNOX differs from ENOX1 and ENOX2 as well as the canonical arNOX by being tightly bound to circulating low density lipoprotein (LDL) particles and carrying out ferricytochrome c reduction which is resistant to inhibition by superoxide dismutase. It also exhibits an inhibitor response pattern different from other ENOX proteins and utilizes lipoprotein particle-bound protein B as its natural substrate. The activity of arNOX, which differs in the above important respects from apoBNOX in aging cells and in sera, has been described previously (Morré and Morré, 2006, Rejuvenation Res. 9: 231-236).

Age and oxidative stress are major risk factors for heart disease (Schmuck et al., 1995, Clin. Chem. 41: 1628-1632). A large body of evidence supports the notion that reactive oxygen species provide a causal link in the appearance of oxidized circulating lipoproteins such as oxidized LDLs and their subsequent clearance by macrophages and delivery to the arterial wall. It now appears likely that oxidized LDL is a major contributor to progressive atherogenesis by enhancing endothelial injury, by inducing foam cell (lipoprotein engorged macrophages) generation and associated smooth muscle proliferation (Halvoet, 1999, Ther. Apher. 3: 287-293). Macrophages clear the circulation of oxidized lipoprotein particles by internalizing them and in so doing are transformed into foam cells. The foam cells deliver their cargo of oxidized fats and cholesterol where they are deposited beneath the arterial wall. Such progressive delivery of oxidatively-damaged lipoprotein particles eventually leads to atherosclerotic plaques and advanced heart disease.

However, the basis for LDL oxidation has been little studied. Levels of common antioxidants including α-tocopherol, β-carotene and ascorbate decline with age but there is no apparent correlation between ingestion of these common antioxidants and amelioration of the aging process or decreased mortality (Bjelakovic et al., 2007, JAMA 294: 842-857). The implication is that the oxidative damage leading to aging and increased atherogenic risk is the result of a much more specific causation. Why does LDL oxidation increase in the elderly and why is it greater in some individuals than in others? Our findings suggest that LDL oxidation in the elderly and in individuals at high risk for heart disease correlates with levels of circulating apoBNOX.

The amount of apoBNOX associated with circulating lipoprotein particles increases starting at about age 30 and reaches maximum at about age 75 in males and age 55-65 in females. Of those who die of a heart attack, 85% are 65 or older (American Heart Association, 2008, Circulation 17: e25-3146). Women surviving beyond age 65 usually have diminished apoBNOX levels compared to men and a lower risk of cardiovascular disease compared to men (Kannel and Lavine, 2003, Prog. Cardiovasc. Nursing 18: 135-140) further suggesting some causal relationship between apoBNOX levels and atherogenic risk.

Consequently, there is a need to find agents that inhibit apoBNOX for the purposes of reducing or treating the resultant physiological conditions, such as oxidation of apoprotein B molecules in low density lipoprotein (LDLs) and attendant arterial changes. The arNOX activity of aging cells has been shown to be inhibited by naturally occurring agents such as coenzyme Q (ubiquinone) including $CoQ_{10}$, $CoQ_9$ and $CoQ_8$ (Morré et al., 2008, BioFactors 32: 231-235); Morré et al., 2003, Mol. Cell. Biochem. 254: 101-109; U.S. Pat. No. 6,878, 514). These agents, however, are relatively ineffective in the inhibition of apoBNOX.

Even if it were an effective inhibitor, the use of coenzyme Q would not completely be satisfactory as an apoBNOX inhibitor for several reasons: it is costly, it oxidizes easily losing its efficacy, and preparations containing coenzyme Q must be specially packaged to prevent loss of function. Thus, there are no economical and chemically stable agents or methods currently known to inhibit apoBNOX activity. Accordingly, it would be an improvement in the art to identify economical and chemically stable agents and techniques with the agents that inhibit apoBNOX but that are also non-toxic and advantageously are naturally occurring.

DEFINITIONS

As used herein, the term "disorder" refers to an ailment, disease, illness, clinical condition, or pathological condition.

As used herein, the term "reactive oxygen species" refers to oxygen derivatives from oxygen metabolism or the transfer of free electrons, resulting in the formation of free radicals (e.g., superoxides or hydroxyl radicals).

As used herein, the term "antioxidant" refers to compounds that neutralize the activity of reactive oxygen species or inhibit the cellular damage done by said reactive species.

As used herein, the term "pharmaceutically acceptable carrier" refers to a carrier medium that does not interfere with the effectiveness of the biological activity of the active ingredient, is chemically inert, and is not toxic to the patient to whom it is administered.

As used herein, the term "pharmaceutically acceptable derivative" refers to any homolog, analog, or fragment which exhibits apoBNOX inhibitory activity. This term includes chemical derivatives as well, such as salts, esters and the like, such that the active ingredient is released, produced or otherwise available after administration.

SUMMARY

The present disclosure relates to a new molecular target for oxidation of apolipoprotein B associated with circulating lipoprotein particles and to agents to inhibit the target molecule and methods for using the same, and more particularly, to inhibitors such as tyrosol and hydroxytyrosol that are present in high amounts in the Mediterranean Diet including both olive oil and white wine, or white wine extracts or concentrates. These several naturally-occurring apoBNOX inhibitors alone, and especially in combinations, can be incorporated into nutritional supplements and/or pharmaceutical compositions to lessen the severity and/or reduce incidence of or to treat disorders and complications of disorders resulting from cell damage caused by the lipoprotein particle-associated apoBNOX molecules. In one exemplary embodiment, these agents comprise at least one naturally occurring apoBNOX inhibitor. In another embodiment, the inhibitor may be administered in a sustained release formulation incorporated in a nutritional supplement or in a pharmaceutical formulation.

Provided herein are pharmaceutical compositions, nutritional supplements, methods of use, and pharmaceutical kits for the treatment of disorders resulting from oxidative changes in cells that result in aging by targeting an aging-related ENOX isoform (apoBNOX) into the sera by aging cells and present tightly associated with the surface of circulating lipoprotein particles.

The present compositions and methods are based, at least in part, on the discovery of an aging-related isoform of NADH oxidase (apoBNOX) directly associated with circulating lipoprotein particles and capable of directly oxidizing the apoprotein B constituents of the particles. The inhibition of apoBNOX results in a decrease in apolipoprotein B oxidation and an attendant decrease in damaged lipoprotein particles and decreased foam cell formation, leading to diminished development of atherogenic plaques.

In another embodiment, the present disclosure provides methods and compositions for screening assays to identify agents that inhibit apoBNOX. In one embodiment, there are methods for inhibition of lipoprotein particle-associated apoBNOX in sera.

The pharmaceutical or nutritional supplement compositions can be used to advantage via varying modes of administration of compounds that inhibit apoBNOX. The modes of administration of compounds includes but is not limited to oral administration (using capsules, tablets, soft gels, solutions), rectal administration (using suppositories), intravenous, intramuscular or intradermal injections, inhalation (aerosols), transdermal administration (transdermal patches or iontophoretic compositions) or a kit for administering in a mode described herein. In yet another embodiment, the present disclosure comprises the methods for isolation of purified apoBNOX and characterization of apoBNOX.

In various other exemplary embodiments, the composition further includes an edible or pharmaceutically acceptable carrier. In some exemplary embodiments, the apoBNOX inhibitory agent is present together with other apoBNOX inhibitors derived from naturally occurring sources including but not limited to olive oil and white wine or white wine extracts. In various exemplary embodiments, apoBNOX inhibitor agents from one source may be augmented by the effects of apoBNOX inhibitory agents from another source.

Those of skill in the art will recognize that the apoBNOX inhibitory compositions described herein can be administered in any convenient manner. In certain exemplary embodiments such forms of administration include gel capsules, tablets or sustained release granules. In these and other exemplary embodiments, the apoBNOX inhibitory agent is provided at a concentration to allow for a daily dose of from between 100 and 600, or between 200 and 600, or between about 100 and 300 mg per day for an adult human.

The magnitude of a therapeutic dose of apoBNOX inhibitor in the acute or chronic management of aging-related oxidative damage varies with the severity of the condition to be treated and the route of administration. The dose and dose frequency also vary according to the age, body weight, condition and response of the individual patient, and the particular combination used. All combinations described herein are encompassed as therapeutic and it is understood that one skilled in the art would be able to determine a proper dosage of particular inhibitor mixtures using the parameters provided herein. In general, the total daily dose ranges of the active materials for the conditions described herein are generally from about 10 mg to about 2000 mg administered in divided doses administered parenterally, orally or topically to an adult human. An exemplary total daily dose is from about 200 mg to about 600 mg.

In various embodiments of the methods provided herein, the apoBNOX inhibitory capsules or tablets are taken orally at least once a day by an adult human.

At least one dosage form is as a sustained release formulation. Preferably, the sustained release formulation is provided in a manner that maintains a constant level of inhibition for at least 12 hours of a 24 hour period in an adult human.

Methods (screening assays) for identifying compounds, agents or compositions that inhibit apoBNOX allow the development of nutritional supplements or pharmaceutical compositions useful for inhibiting apoBNOX and thus, reducing or ameliorating the effects of apoB and/or LDL oxidation, with the benefit that cardiovascular disease is delayed or decreased in severity. These screening assays may be based on the use of recombinant apolipoprotein B, purified naturally occurring proteins and/or synthetic peptides, for example an apoB-derived peptide comprising, consisting essentially of or consisting of the amino acid sequence FHCRDGNCIHNHWQCDGDYDCGEGSDE (SEQ ID NO:3) or a sequence with at least 50%-99% identity thereto which serves as a substitute for the apoBNOX protein. In such assays, apoBNOX activity is measured in the presence and absence of a test compound in apoNOX and apoB (or analog) containing reaction mixtures. Those compounds, agents or compositions that inhibit apoBNOX are identified as those resulting in less oxidation or lower rates of oxidation of apoB or its equivalent in the assay, including where the reaction is monitored via NADH oxidation or ferricytochrome c reduction.

In an embodiment, the invention encompasses methods for inhibition of lipoprotein-particle-associated apoBNOX in sera. In other embodiments, the invention encompasses methods for inhibition of apoBNOX purified from lipoproteins of sera or replaced by an appropriate synthetic peptide. With the first embodiment, the source of apoBNOX can be apoBNOX normally present in sera. In the other embodiments, the apoBNOX can be apoBNOX purified from sera or lipoprotein particles isolated from sera or preferably the apoBNOX source is recombinant protein expressed in bacteria transfected with apoBNOX cDNA.

Provided as well is a synthetic peptide which can serve as an apoB replacement in apoBNOX assays. The peptide comprises the sequence FHCRDGNCIHNHWQCDGDYDCGEGSDE (SEQ ID NO:3), or a sequence with at least about 50%, 75%, 92%, 96%, 97%, 98% or 99% identity thereto.

These and other features and advantages of the present compositions and methods are set forth below or will become more fully apparent in the description that follows and in the appended claims. The features and advantages may be realized and obtained by means of the formulations and combinations particularly pointed out in the appended claims. Furthermore, the features and advantages of the present methods and compositions may be learned by the practice of the invention or will be apparent from the description, as set forth hereinafter.

BRIEF DESCRIPTION OF THE FIGURES

Various exemplary embodiments of the composition and methods provided herein will be described in detail, with reference to the following figures wherein:

FIG. 5. Unique amino acid sequence and functional motifs of apoBNOX. The amino acid sequence of the protein is given in SEQ ID NO:2 and the coding sequence is given in SEQ ID NO:1.

DETAILED DESCRIPTION

The present disclosure provides pharmaceutical or cosmetic compositions, methods of use, and pharmaceutical kits for the treatment of disorders resulting from oxidative changes in cells that result in aging by targeting an aging-related isoform of NADH oxidase (apoBNOX) associated with circulating lipoprotein particles. The compositions may contain agents extracted from common dietary ingredients. For example, the compositions described herein may comprise at least one extract shown to inhibit apoBNOX activity, whether alone or with other inhibition agents and, inhibit or block its activity. The composition may comprise natural extracts or agents derived therefrom known to comprise active agents useful in inhibiting apoBNOX together with other compounds known to the art. Such other compounds may comprise gums, fillers, preservatives and the like.

Figure 4:
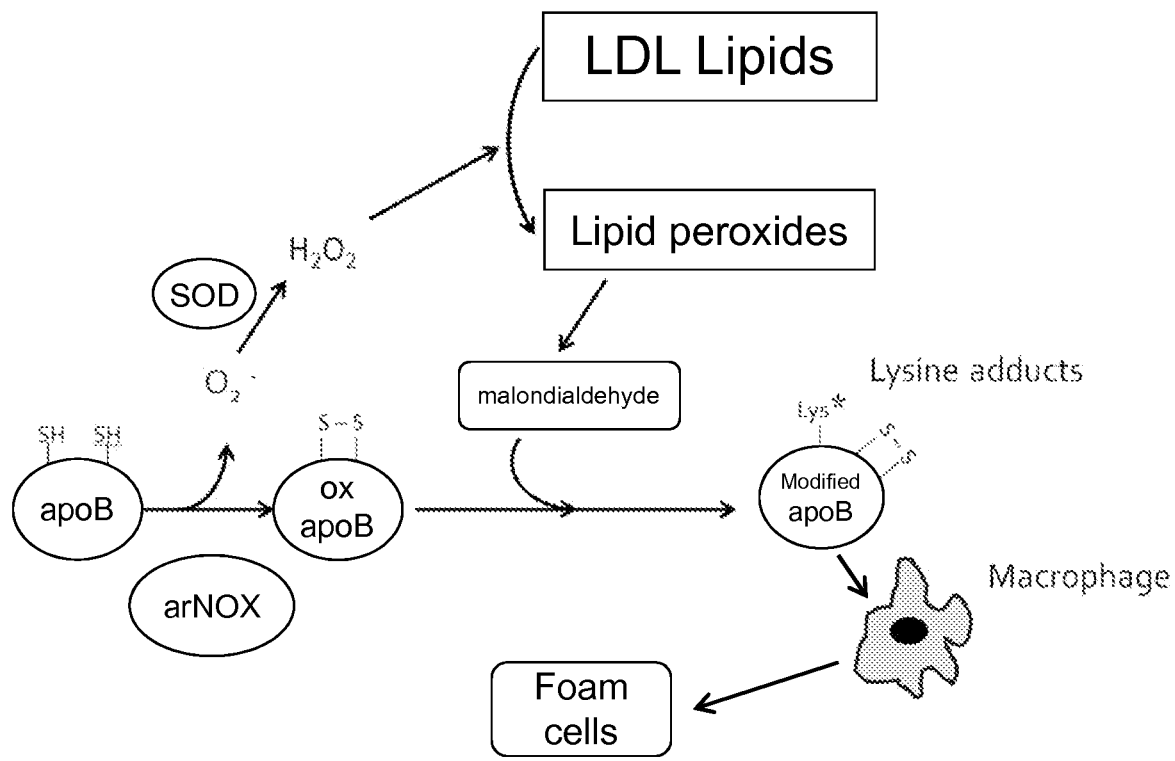
FIG. 4. Scheme illustrating the role of apoBNOX in oxidation of apoB associated with low density lipoprotein particles.

FIG. 4 illustrates the role of apoBNOX in the oxidation of the apoB protein associated with low density lipoprotein particles and the recognition of the oxidized LDL by macrophages, resulting in the formation of foam cells leading to fatty streaks and atherogenic plaques. In this scheme, the apoBNOX binds selectively to lipoprotein particle-associated apoB and withdraws electrons to form superoxide. Evidence that the source of these electrons is protein thiols is given in Table 1. The superoxide thus generated is converted to hydrogen peroxide by the action of superoxide dismutase. The hydrogen peroxide thus generated attacks lipids (particularly phosphatidylcholine) of the low density lipoprotein particles to form reactive lipid peroxides that then attack key lysine residues in the apoB. Evidence that superoxide generated by arNOX when converted to hydrogen peroxide is capable of oxidizing phosphatidylcholine is given by the data of Table 2.

TABLE 1

Lipid oxidation catalyzed by $H_2O_2$ formed from recombinant arNOX-generated superoxide.

| Incubated 2 h | Relative units cm | | $H_2O_2$ equivalent μmoles/mg |
|---|---|---|---|
| SF2[1] + lecithin + SOD | 0.12 | 0.06 | 1.3 |
| SF2 + lecithin + SOD + CoQ[2] | 0.06 | | |
| SF2 + lecithin + SOD + 3-way inhibitor[3] | 0.06 | | |
| SF2 + lecithin | 0.06 | | |
| SF4[1] + lecithin + SOD | 0.10 | 0.06 | 1.3 |
| SF4 + lecithin +SOD + CoQ | 0.04 | | |
| SF4 + lecithin + SOD + 3-way inhibitor | 0.04 | | |
| SF4 + lecithin | 0.04 | | |
| Saliva + lecithin + SOD | 0.3 | 0.18 | 4.0 |
| Saliva + lecithin + SOD + CoQ | 0.12 | | |
| Saliva + lecithin | 0.12 | | |
| Saliva + lecithin + SOD + 3-way inhibitor | 0.12 | | |

[1]100 ng/25 μl; 250 μl = 1 μg recombinant SF-4
[2]To 2.5 ml of 255 volume were added 2.5 μl of 100 mM coenzyme $Q_{10}$ in ethanol
[3]To 2.5 ml of assay volume were added 25 μl of an aqueous mixture of 4 mg/ml *Schizandra chinensis* extract, 9% Schizandrins, Draco, San Jose, CA) plus 1 mg/ml salicin (Sigma-Aldrich, St. Louis, MO) and 20 μl of IBR Dormin (Israeli Biotechnology Research, Ramat-Gan, Israel).

TABLE 2

Oxidation of protein thiols of human apoB purified from serum LDL by
recombinant arNOX SF-2 and SF-4 and saliva (75 y male).

|  | Relative units | nmoles SH oxidized[3] |
|---|---|---|
| Complete | 25 | 500 |
| apo B[1] | 9 | 180 |
| SF2[2] | 0 | 0 |

[1]160 µg human apoB purified from LDL = 16 µg cysteine thiol = 1,333 nmoles
[2]0.2 µg recombinant arNOX SF2
[3]Based on DTNB (dithiodinitrobenzoic acid) reactivity of cysteine standards. Incubation time of 2 h. Oxidation of 500 nmoles SH generated 250 nmoles $H_2O_2$.

Figure 6:
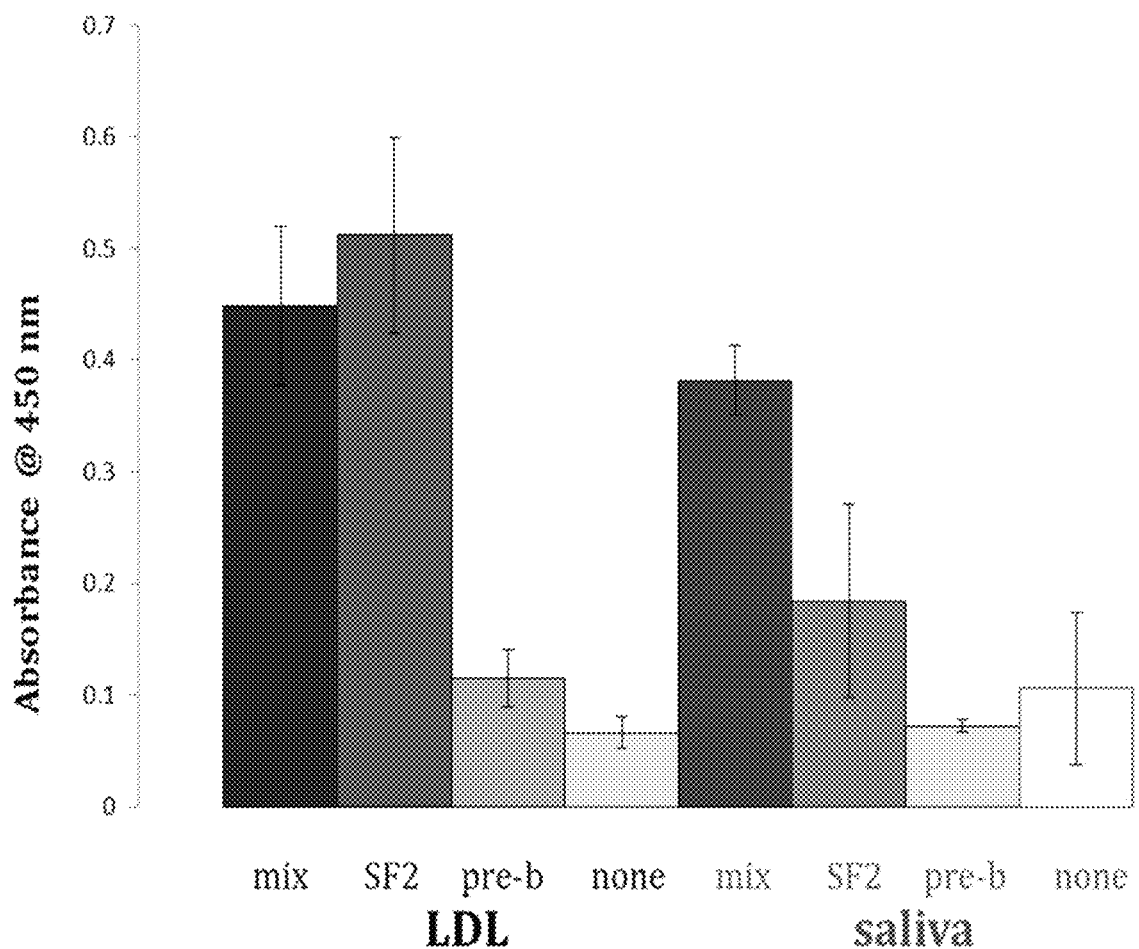
FIG. 6. ELISA analysis of arNOX isoforms of LDL (left) compared to saliva (right). In contrast to saliva, with LDL nearly all of the arNOX reacts with a specific antibody to isoform SF2 (=apoBNOX) compared to a mixture of antibodies to all 5 arNOX isoforms (mix).
Figure 7:
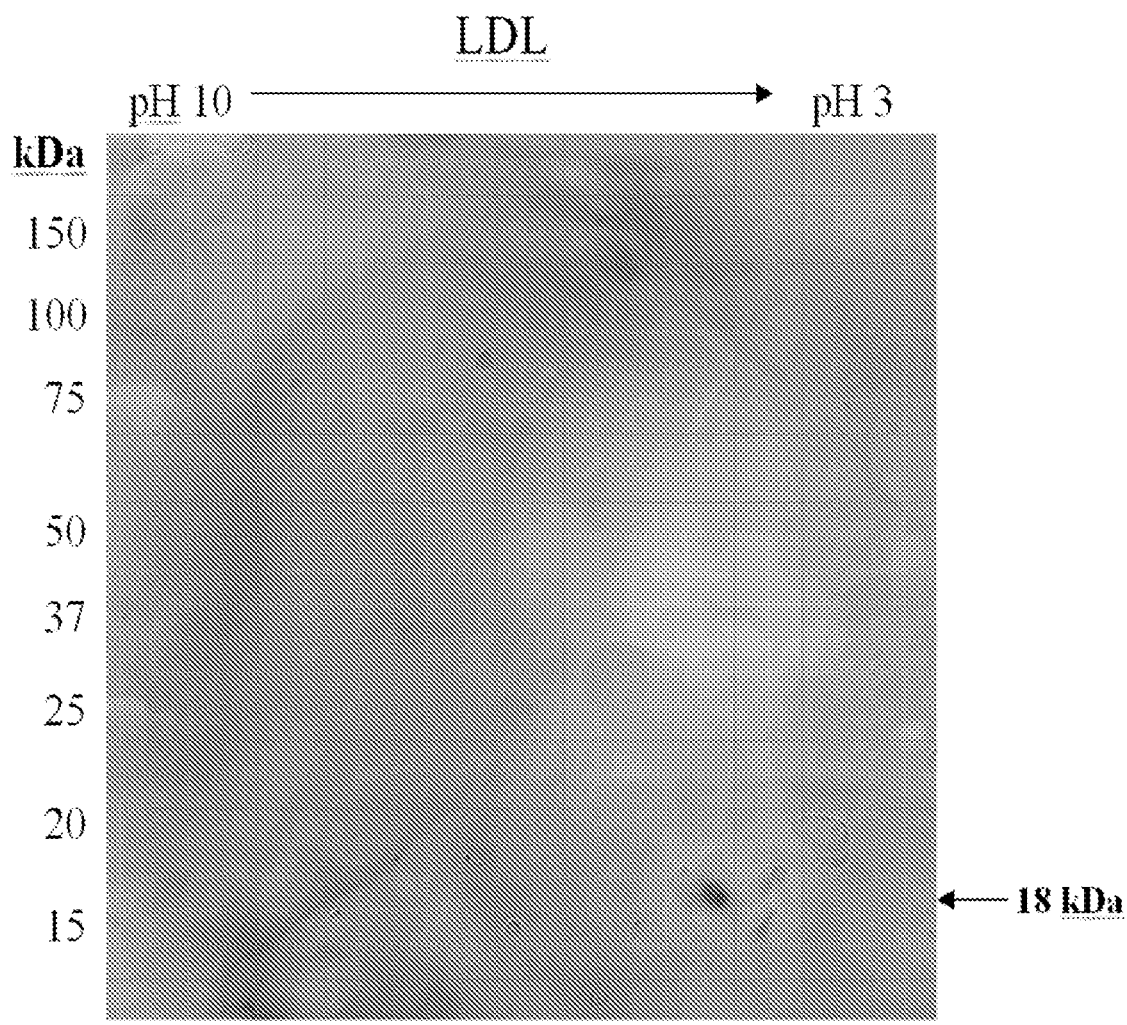
FIG. 7. 2-D gel electrophoresis and western blot with antibody to TM9 SF2 (apoBNOX) showing the presence of a ca. 18 kDa soluble fragment associated with low density lipoprotein particles purified from human sera.

That apoBNOX is a unique arNOX form related to atherogenesis is implicit in the sequence of apoBNOX (FIG. 5) also known as TM9 SF2 (GenBank accession number U81006; WO 2011/022387; see also SEQ ID NO:2 herein). The C-terminus of apoBNOX which is shed into the circulation contains a peptide sequence of 25 amino acids with 56% similarity with the LDL receptor binding surface. Without wishing to be bound by theory, it is believed that this allows for the tight binding of the apoBNOX to the exposed binding surface of the apoB of the lipoprotein particles. As a result of the tight binding, nearly 50% of the total arNOX activity (Table 3) and nearly all of the TM9 SF2 (apoBNOX) (FIG. 6) of human sera or plasma co-purifies with LDL upon flotation centrifugation through dilute salt solutions or distilled water. Truncated TM9 SF2 (apoBNOX) is present in isolated LDL as shown by 2-D gel electrophoresis and western blotting with TM9 SF2⁻ (apoBNOX⁻) specific antisera (FIG. 7). Comparing preparations of LDL from subjects with low and high LDL levels (Table 4), apoBNOX levels determined by immune absorbance enzyme linked assay (ELISA) correlated with total arNOX activity further demonstrating the specific association between apoBNOX and lipoprotein particles of sera. Tight binding is also evidenced by co-isolation of apoB and apoBNOX via size exclusion chromatography. These findings together with the property of the apoBNOX associated with lipoprotein particles to resist inhibition by superoxide dismutase and coenzyme $Q_{10}$ as well as other water-soluble arNOX inhibitors such as savory infusion and apigenin and its other active constituents point to the uniqueness of the TM9 SF1 arNOX form in support of its special designation as apoBNOX.

TABLE 3 arNOX is lipoprotein-associated. apoBNOX-mediated oxidation
of apoprotein B of serum lipoproteins was determined from rate of
ferricytochrome c reduction with lipoprotein particles
isolated by flotation centrifugation of sera of human
subjects with low vs. elevated LDL amounts.

|  | Nmoles/min/ml | | Lipoprotein bound, % of total activity | |
|---|---|---|---|---|
|  | Elevated LDL | Low LDL | Elevated LDL | Low LDL |
| Serum | 1.0 | 0.6 | 32 | 20 |
| Plasma | 1.2 | 1.0 | 43 | 27 | arNOX-mediated oxidation of apoprotein B of serum lipoproteins was determined from rate of ferricytochrome c reduction with lipoprotein particles isolated by flotation centrifugation of sera and plasma of human subjects with low vs. elevated LDL amounts.

TABLE 4

Correlation between ELISA absorbance using apoBNOX
antibody (FIG. 6) and arNOX activity based on superoxide
generation measured from a standard assay using ferricytochrome c
reduction comparing sera of subjects with low and high levels of LDL.

|  | ELISA absorbance Blank | arNOX activity Ferricytochrome c reduction, nmoles/min/100 µl |
|---|---|---|
| Low LDL | 0.09 | 0.045 |
| High LDL | 0.23 | 0.12 |
| Ratio High/Low LDL | 2.6 | 2.7 |

EXAMPLES

Example 1

Characterization of apoBNOX Inhibitors

Reduction of ferricytochrome c by superoxide was employed as the measure of superoxide dismutase-resistant apoBNOX activity (Mayo, L. A. and Curnutte, J., 1990, Meth. Enzyme. 186: 567-575; Butler, J. et al., 1982, J. Biol. Chem. 257: 10747-10750). The assay consists of 150 µl buffy coats in PBSG buffer (8.06 g NaCl, 0.2 g KCl, 0.18 g $Na_2HPO_4$, 0.13 g $CaCl_2$, 0.1 $MgCl_2$, 1.35 g glucose dissolved in 1000 ml deionized water, adjusted to pH 7.4, filtered and stored at 4° C.). Rates were determined using an SLM Aminco DW-2000 spectrophotometer (Milton Roy, Rochester, N.Y.) in the dual wave length mode of operation with continuous measurements over 1 min every 1.5 min. After 45 min, test compounds were added and the reaction was continued for an additional 45 min. After 45 min, a millimolar extinction coefficient of 19.1 $cm^{-1}$ was used for reduced ferricytochrome c. The results from a typical test compound effective in inhibiting apoBNOX are provided in Table 5.

TABLE 5 apoBNOX activity inhibition by 100 µM tyrosol
(4-hydroxylphenethyl alcohol) and white wine extract.

| Substance or extract |  | apoBNOX activity, % inhibition |
|---|---|---|
| Tyrosol | 100 µM | 70% |
| White wine | Concentrated extract | 65% |

Inhibition by 100 µM tyrosol or white wine concentrate in the assay was about 65-70%.

Example 2

Kinetics of apoBNOX

By incorporating sustained release agents in the tyrosol, hydroxytyrosol and/or white wine extract formulations, it is possible to achieve 12 h protection from a two capsule/day regimen with the possibility of extending the regimen to a one capsule/day 24 h protection regimen. This is a further unique aspect of the present methods in that makes possible a therapeutic utility of the technology of importance to treating aging-related damage from oxidized circulating lipoproteins in individuals as they age beyond 30 years.

Example 3 apoBNOX Activity Associated with Serum Lipoprotein Particles

That the apoBNOX activity is associated with lipoprotein particles of sera was demonstrated from data of Table 3.

Example 4

Correlation of apoBNOX Activity and Apoprotein B Oxidation

Figure 1:
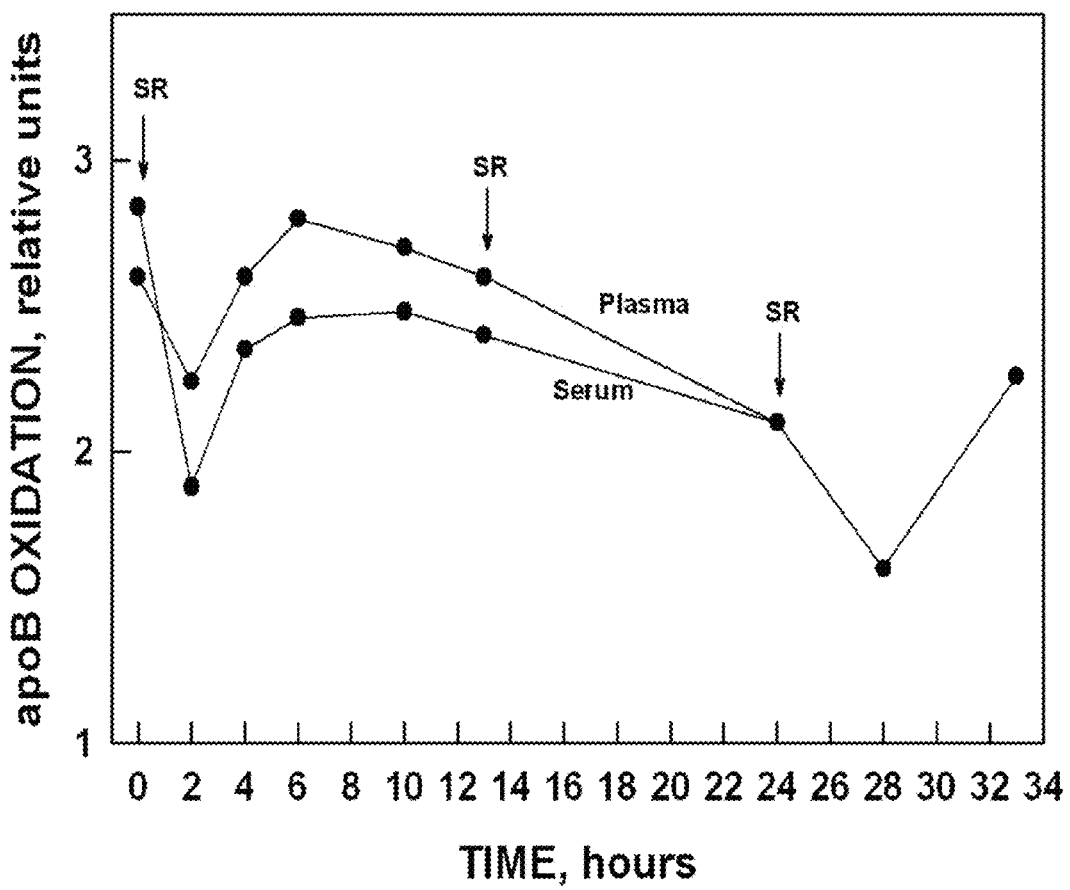
FIG. 1. Time course of serum apoBNOX activity of a 73 y male subject after oral administration of an appropriate sustained release (SR) apoBNOX inhibitor administered daily based on decreased amounts of circulating oxidized lipoprotein B determined by an ELISA assay specific for oxidized lipoprotein B (Mercodia).
Figure 2:
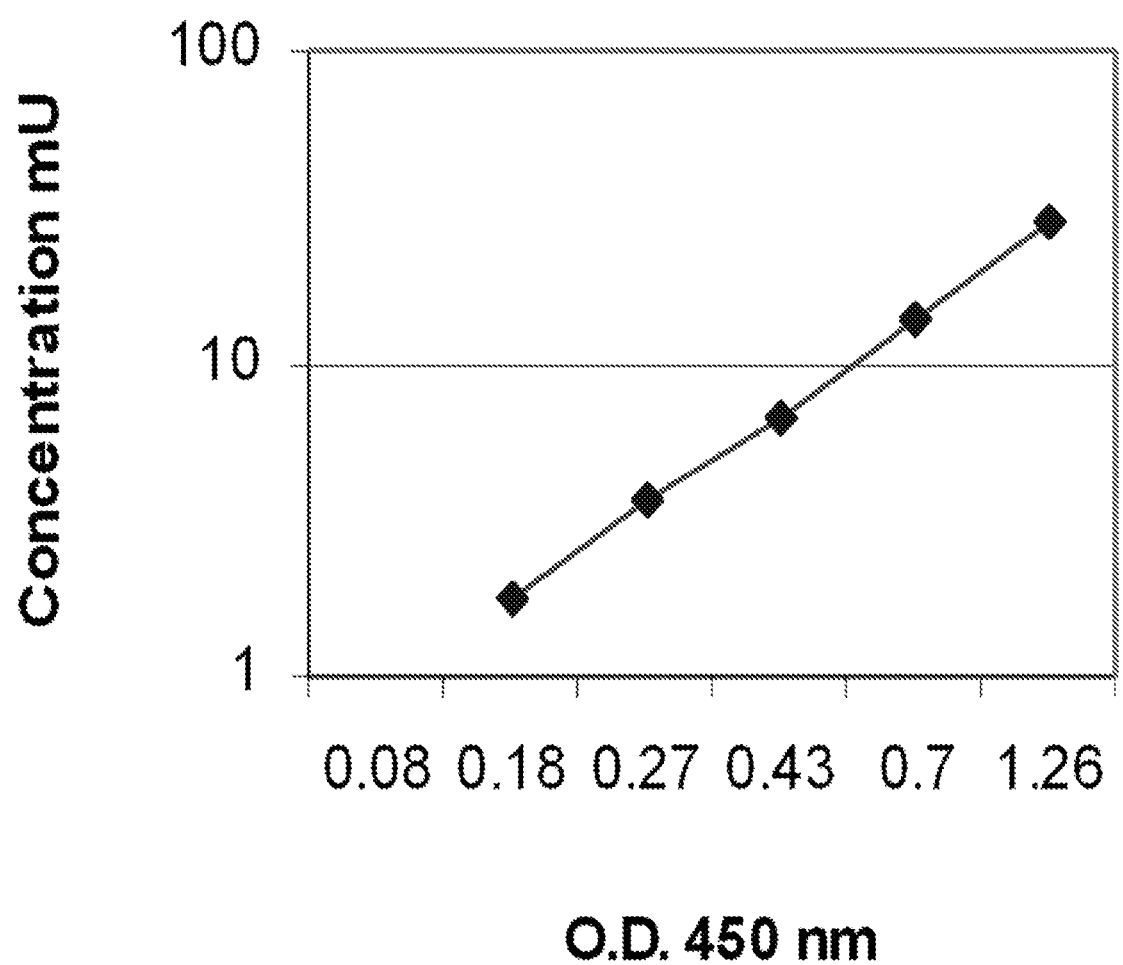
FIG. 2. Calibration curve for determining the amount of oxidized apoprotein B using the ELISA method of FIG. 1.
Figure 3:
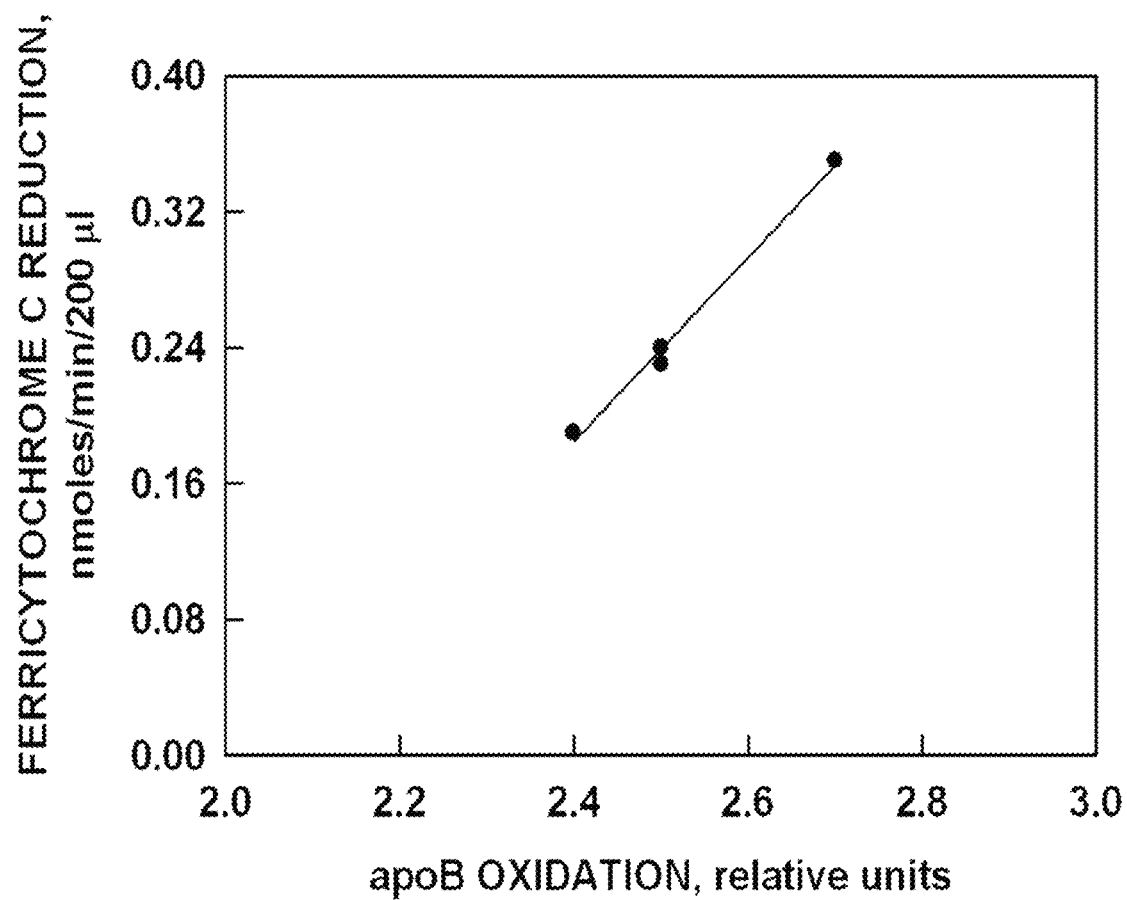
FIG. 3. Correlation between ferricytochrome c reduction as a measure of apoBNOX activity and levels of oxidized apoprotein B in sera and plasma of four laboratory volunteers.

FIG. 3 shows a correlation between apoBNOX activity and protein B oxidation for sera and plasma of four laboratory volunteers.

Example 5

Expression of Recombinant apoBNOX pET11a vector and *Escherichia coli* BL21 (DE3) competent cells were purchased from Novagen (Madison, Wis.). I.M.A.G.E. Full length cDNA IRAUp969E0589D was from ImaGenes (Berlin, Germany).

Plasmids carrying TM9SF2 sequence were prepared by inserting the pET11a vector (between NheI and BamHI sites) with TM9SF2 sequence. The TM9SF2 sequence was synthesized by GenScript USA Inc. (Piscataway, N.J.).

DNA sequences of the ligation products (pET11a-TM9SF2) were confirmed by DNA sequencing. Then pET11a-TM9SF2 was transformed to *E. coli* BL21 (DE3) competent cells. A single colony was picked and inoculated into the 5 ml LB/AMP medium. The overnight culture (1 ml) was diluted into 100 ml LB/AMP media (1:100 dilution). The cells were grown with vigorous shaking (250 rpm) at 37° C. to an OD600 of 0.4-0.6 and IPTG (0.5 mM) was added for induction. Cultures were collected after 5 h shaking (250 rpm) at 37° C. Expression of the TM9SF2 was confirmed by SDS-PAGE with silver staining.

Cultures were centrifuged at 6,000 g for 20 min. Pellets were resuspended in 20 mM Tris-Cl, pH 8.0 (0.5 mM PMSF added). Cells were broken by French Press at 20,000 psi 3 times.

The extracts were centrifuged at 10,000 rpm for 20 min. Supernatant was discarded and pellets (inclusion bodies) were resuspended in 20 ml of Tris buffer. Two ml of 20% Triton X-100 was added to each tube and sample volume was adjusted to 40 ml with Tris buffer. Tubes were incubated at room temperature for 1 h with shaking and centrifuged at 10,000 rpm for 20 min. Supernatants were discarded and pellets were washed two times with Tris buffer by resuspending in 25 ml of Tris buffer and centrifuged one time with 25 ml of pure water.

For solubilization of the inclusion bodies, pellets were resuspended in 20 ml of water and 4 ml of 0.5 M CAPS buffer, pH 11 (50 mM final concentration), 40 µl of 1 M DTT (1 mM final concentration) and 0.4 ml of 30% sodium lauryl Sarcosine (0.3% final concentration) were added. Sample volumes were adjusted to 40 ml with water. Samples were incubated at room temperature for 17 h.

TABLE 6

| Transmembrane 9 superfamily member 2 (*Homo sapiens*) (SEQ ID NO: 1) | | |
|---|---|---|
| VERSION | NP_004791.1 GI: 4758874 | |
| DBSOURCE | REFSEQ: accession NM_004800.1 | |

```
   1 cgcaaccgga actagccttc tggggccgg cttggtttat ctctggcggc cttgtagtcg
  61 tctccgagac tccccacccc tccttccctc ttgacccct aggtttgatt gccctttccc
 121 cgaaacaact atcatgagcg cgaggctgcc ggtgttgtct ccacctcggt ggccgcggct
 181 gttgctgctg tcgctgctcc tgctgggggc ggttcctggc ccgcgccgga gcggcgcttt
 241 ctacctgccc ggcctggcgc ccgtcaactt ctgcgacgaa gaaaaaaga gcgacgagtg
 301 caaggccgaa atagaactat ttgtgaacag acttgattca gtggaatcag ttcttcctta
 361 tgaatacaca gcgtttgatt tttgccaagc atcagaagga aagcgcccat ctgaaaatct
 421 tggtcaggta ctatcgggg aaagaattga accttcacca tataagttta cgtttaataa
 481 gaaggagacc tgtaagcttg tttgtacaaa aacataccat acagagaaag ctgaagacaa
 541 acaaaagtta gaattcttga aaaaaagcat gttattgaat tatcaacatc actggattgt
 601 ggataatatg cctgtaacgt ggtgttacga tgttgaagat ggtcagaggt tctgtaatcc
 661 tggatttcct attggctgtt acattacaga taaaggccat gcaaaagatg cctgtgttat
 721 tagttcagat ttccatgaaa gagatacatt ttacatcttc aaccatgttg acatcaaaat
 781 atactatcat gttgttgaaa ctgggtccat gggagcaaga ttagtggctg ctaaacttga
 841 accgaaaagc ttcaaacata cccatataga taaaccagac tgctcagggc cccccatgga
 901 cataagtaac aaggcttctg gggagataaa aattgcctat acttactctg ttagcttcga
 961 ggaagatgat aagatcagat gggcgtctag atgggactat attctggagt ctatgcctca
1021 tacccacatt cagtggttta gcattatgaa ttccctggtc attgttctct tcttatctgg
```

TABLE 6-continued

Transmembrane 9 superfamily member 2 (*Homo sapiens*) (SEQ ID NO: 1)

| VERSION | NP_004791.1 GI: 4758874 |
|---|---|
| DBSOURCE | REFSEQ: accession NM_004800.1 |

```
1081  aatggtagct atgattatgt tacggacact gcacaaagat attgctagat ataatcagat
1141  ggactctacg gaagatgccc aggaagaatt tggctggaaa cttgttcatg gtgatatatt
1201  ccgtcctcca agaaaaggga tgctgctatc agtctttcta ggatccggga cacagatttt
1261  aattatgacc tttgtgactc tatttttcgc ttgcctggga tttttgtcac ctgccaaccg
1321  aggagcgctg atgacgtgtg ctgtggtcct gtgggtgctg ctgggcaccc ctgcaggcta
1381  tgttgctgcc agattctata agtcctttgg aggtgagaag tggaaaacaa atgttttatt
1441  aacatcattt ctttgtcctg ggattgtatt tgctgacttc tttataatga atctgatcct
1501  ctggggagaa ggatcttcag cagctattcc ttttgggaca ctggttgcca tattggccct
1561  ttggttctgc atatctgtgc ctctgacgtt tattggtgca tactttggtt taagaagaa
1621  tgccattgaa cacccagttc gaaccaatca gattccacgt cagattcctg aacagtcgtt
1681  ctacacgaag cccttgcctg gtattatcat gggagggatt ttgccctttg gctgcatctt
1741  tatacaactt ttcttcattc tgaatagtat ttggtcacac cagatgtatt acatgtttgg
1801  cttcctattt ctggtgttta tcatttggt tattacctgt tctgaagcaa ctatacttct
1861  ttgctatttc cacctatgtg cagaggatta tcattggcaa tggcgttcat tccttacgag
1921  tggctttact gcagtttatt tcttaatcta tgcagtacac tacttctttt caaaactgca
1981  gatcacggga acagcaagca caattctgta ctttgttat accatgataa tggttttgat
2041  cttctttctt tttacaggaa caattggctt ctttgcatgc ttttggtttg ttaccaaaat
2101  atacagtgtg gtgaaggttg actgaagaag tccagtgtgt ccagttaaaa cagaaataaa
2161  ttaaactctt catcaacaaa gacctgtttt tgtgactgcc ttgagtttta tcagaattat
2221  tggcctagta atccttcaga aacaccgtaa ttctaaataa acctcttccc atacacctttt
2281  cccccataag atctgtcttc aacactataa agcatttgta ttgtgatttg attaagtata
2341  tatttggttg ttctcaatga agagcaaatt taaatattat gtgcatttga a
```

TABLE 7

Transmembrane 9 superfamily member 2 (*Homo sapiens*)(SEQ ID NO: 2)

```
1msarlpvlsp prwprllls lllgavpgp rrsgafylpg lapvnfcdee kksdeckaei
61elfvnrldsv esvlpyeyta fdfcqasegk rpsenlqqvl fqeriepspy kftfnkketc
121klvctktyht ekaedkqkle flkksmllny qhhwivdnmp vtwcydvedg qrfcnpgfpi
181gcyitdkgha kdacvissdf herdtfyifn hvdikiyyhv vetgsmgarl vaaklepksf
241khthidkpdc
```

Conserved CQ/CE
Adenine nucleotide binding site GXVXXG at amino acids 97-102
Putative protein disulfide interchange site CXXXC
Putative copper sites YQH and HTH Example 6

Refolding of Recombinant apoBNOX

After solubilization, samples were centrifuged at 10,000 rpm for 20 min and supernatants were collected. The supernatants were filtered through 0.45 μm syringe filter. The filtrates were poured into two dialysis bags (3,500 MWCO, flat width 45 mm and diameter 29 mm, SpectraPor) and dialyzed against cold dialysis buffer A (25 mM Tris-HCl, pH 8.5, 1 mM cysteamine, 0.1 mM cysteamine, 1 mM 6-aminocaproic acid and 0.5 mM benzamidine HCl) with 3 changes, against cold dialysis buffer B (25 mM Tris-HCl, pH 8.0, 1 mM 6-aminocaproic acid and 0.5 mM benzamidine HCl) with one change and against dialysis buffer C (50 mM Tris-HCl, pH 8.0, 1 mM 6-aminocaproic acid and 0.5 mM benzamidine HCl) with one change. Dialysis was at least 17 h for each change. After dialysis, PMSF was added to final concentration of 0.5 mM and samples were centrifuged at 10,000 rpm for 20 min. Supernatant was collected and concentrated to about 16 ml by using Centriplus Concentrator (Amicon, MWCO 10,000, 470 rpm, 2800×g). Refolded arNOX was aliquoted to 0.5 ml into microcentrifuge tubes and stored at −80° C.

Example 7

Measurement of apoBNOX Activity arNOX activity was assayed from measurements of superoxide production based on a standard method where reduction of ferricytochrome c was monitored from the increase in absorbance at 550 nm with reference at 540 nm (Butler et al., 1982). As a further check for the specificity of the apoBNOX activity, 60 units of superoxide dismutase (SOD) were added near the end of the assay to ascertain that the rate returned to base line. Rates were determined over 1 min at intervals of 1.5 min using a SLM Aminco DW 2000 spectrophotometer (Milton Roy, Rochester, N.Y.) in the dual wavelength mode of operation. An extinction coefficient of 19.1 mM$^{-1}$ cm$^{-1}$ was used for reduced ferricytochrome c.

Oxidation of NADH was determined spectrophotometrically from the disappearance of NADH measured at 340 nm in a reaction mixture containing 25 mM Tris-Mes (pH 7.2), 100 μM GSH, 1 mM KCN to inhibit mitochondrial oxidase activity, 150 μM NADH, and the enzyme at 37° C. with temperature control (±0.5° C.) and stirring. Prior to assay, 1 μM reduced glutathione was added to reduce the protein in the presence of substrate. After 10 min, 0.03% hydrogen peroxide was added to reoxidize the protein under renaturing conditions and in the presence of substrate to start the reaction. Activities were measured using a Hitachi U3210 spectrophotometer with continuous recording. Assays were for 1 min and were repeated on the same sample at intervals of 1.5 min for the times indicated. An extinction coefficient of 6.22 mM-1 cm-1 was used to determine specific activity.

Proteins were estimated by the bicinchoninic acid method with bovine serum albumin was the standard.

Example 8

Isolation of Low Density Lipoproteins and Purification of apoB

Lipoproteins were obtained from sera of normal human volunteers by flotation centrifugation (55,000 rpm in a Beckman L8-70 for 16 h at 4° C., salt density>1.05 g/ml). The LDL was dialyzed for 24 h against 3-4 changes of 0.1 M sodium bicarbonate, pH 8.6 and solubilized with sodium deoxycholate (1.1 g/2 ml) with gentle stirring in the dark. The solubilized dilapidated apoB was applied to a Sepharose CL-4B column. The apoB-containing fractions from the column were pooled and concentrated by ultrafiltration with Amicon YM-10 filters.

All references cited herein are hereby incorporated by reference in their entireties to the extent they are not inconsistent with the present disclosure. References cited herein reflect the levels of skill in the art(s) to which the present disclosure relates.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

Tyrosol or hydroxytyrosol and white wine components, for example in the form of wine wine extract or concentrate, can provide health benefits when provided at a daily dose of 50-600, or about 100-300 mg per day for an adult human. These materials are found within the French and Mediterranean diets (and in olive oil) in significant amounts and may contribute to the so-called French paradox of relatively low cardiovascular disease despite a fairly rich diet. Other apoBNOX inhibitory agents, as identified in the screening assays provided herein, can be also formulated for human supplements or pharmaceutical compositions, using similar dosages or dosages sufficient to provide similar apoBNOX inhibition.

Tyrosol and hydroxytyrosol can be formulated in nutritional supplements or pharmaceutical compositions as esters with pharmaceutically acceptable acids, for example, fatty acids. Illustrations of some hydroxytyrosol and tyrosol derivatives included in this invention include those esterified with fatty acids of 1 to 16 and others. Hydroxyl groups may be protected, for example, an acetic acid chain via an ester bond, as well. Useful compounds include (3,4-Dihydroxyphenyl) ethyl oleate, 2-(3,4-Dihydroxyphenyl)ethyl stearate, 2-(3,4-Dihydroxyphenyl)ethyl docosahexaenoate, 2-(3,4-Dihydroxyphenyl)ethyl eicosapentaenoate, 2-(4-Hydroxyphenyl) ethyl acetate, 2-(4-Hydroxyphenyl)ethyl oleate, 2-(4-Hydroxyphenyl)ethyl stearate, 2-(4-Hydroxyphenyl)ethyl docosahexaenoate, 2-(4-Hydroxyphenyl)ethyl eicosapentaenoate, 2-(3,4-Diacetoxyphenyl)ethyl acetate, 2-(3,4-Dioleyloxyphenyl)ethyl oleate, 2-(3,4-Distearyloxyphenyl)ethyl stearate, 2-(3,4-Didocosahexaenoyloxyphenyl)ethyl docosahexaenoate, 2-(3,4-Dieicosapentaenoyloxyphenyl)ethyl eicosapentaenoate, 2-(4-Acetoxyphenyl)ethyl acetate, 2-(4-Oleyloxyphenyl)ethyl oleate, 2-(4-Stearyloxyphenyl)ethyl stearate, 2-(4-Docosahexaenoyloxyphenyl)ethyl docosahexaenoate, 2-(4-Eicosapentaenoyloxyphenyl)ethyl eicosapentaenoate, Hydroxytyrosol and tyrosol are sensitive to oxidation and are hydrophilic. This last characteristic might be problematic if hydroxytyrosol or tyrosol are pretended to be used in fat-based food products or supplements. Oxidation of hydroxytyrosol and tyrosol clearly affect the stability and preservation of both compounds. The hydroxytyrosol and tyrosol derivatives presented in this invention avoid these two problems. The hydroxyl groups on these derivatives are protected from oxidation by preparing hydroxytyrosol or tyrosol fatty acid esters. When compared to hydroxytyrosol and tyrosol, the hydroxytyrosol and tyrosol fatty acid esters are much more resistant against oxidation. At the same time, depending on the length of the fatty acid chain of the fatty acid esters, their solubility in fat-based food products will be increased. Hydroxytyrosol or tyrosol esters with a wide range of solubilities can be prepared, from totally water-soluble hydroxytyrosol or tyrosol derivatives when acetic acid is used in the formation of the ester to totally oil-soluble hydroxytyrosol or tyrosol derivatives when oleic acid is used in the formation of the ester. The hydroxytyrosol and tyrosol derivatives are hydrolyse in the intestinal tract of rats to their two components, hydroxytyrosol or tyrosol and the fatty acid. Hydroxytyrosol or tyrosol are then rapidly absorbed, being detected in plasma and cerebrospinal fluid. This implies that, after their hydrolysis, mentioned fatty acid esters can act as antioxidants to reduce or ameliorate diseases with an oxidative stress origin.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, starting materials, synthetic methods, and pharmaceutically acceptable carriers, adducts, salts and compositions other than those specifically exemplified can be employed in the practice of the invention without resort to undue experimentation. All art-known functional equivalents, of any such methods, starting materials, synthetic methods, and pharmaceutically acceptable carriers, salts, adducts and compositions are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The following definitions are provided to clarify their specific use in the context of the invention.

The exact formulation, route of administration and dosage can be chosen by the individual physician in view of the patient's condition (see e.g. Fingl et. al., in The Pharmacological Basis of Therapeutics, 1975, Ch. 1 p. 1).

It should be noted that the attending physician would know how to and when to terminate, interrupt, or adjust administration due to toxicity, organ dysfunctions, or other deleterious effects. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration are well known to the art. Suitable routes may include, for example, oral, rectal, transdermal, vaginal, transmucosal, or intestinal administration; parenteral delivery, including intramuscular, or subcutaneous injections, as well as intrathecal, intravenous, intraperitoneal injections, or transdermal administration.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present methods include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions provided herein may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

What is claimed is:

1. A method of identifying an inhibitor of apolipoprotein B NADH oxidase (apoBNOX), said method comprising the steps of:
   a) contacting a biological sample comprising apoBNOX and apolipoprotein B with a test compound in vitro to produce a contacted sample;
   b) measuring apoBNOX activity in the contacted sample of step (a); and
   c) identifying the test compound as an inhibitor of apoBNOX when the apoBNOX activity measured in step (b) is less than the apoBNOX activity of a comparison in vitro biological sample that has not been contacted with the test compound.

2. The method of claim 1, wherein the apoBNOX activity is measured and identified as a reduction of ferricytochrome c.

3. The method of claim 1, wherein the apoBNOX activity is measured by a reduction of NADH which is determined spectrophotometrically and identified as a decrease in absorbance at 340 nm.

4. The method of claim 1, wherein the apolipoprotein B is provided in step (a) as low density lipoprotein particles.

5. The method of claim 1, wherein the apolipoprotein B in step (a) is purified from low density lipoprotein particles.

6. The method of claim 1, where the apolipoprotein B is provided in step a) as an equivalent peptide corresponding to the cellular binding region that normally forms a complex with apoBNOX and restricts access of the majority of arNOX inhibitors to the apoBNOX catalytic site.

7. The method of claim 6, wherein the equivalent peptide comprises the amino acid sequence set forth in SEQ ID NO:3 or an amino acid sequence with at least 50%, 75%, 80%, 92%, or 96% amino acid identity thereto.

8. The method of claim 1, wherein the apoBNOX is bound to the apolipoprotein B.

* * * * *

UNITED STATES PATENT AND TRADEMARK OFFICE
CERTIFICATE OF CORRECTION

PATENT NO.       : 8,465,939 B2
APPLICATION NO.  : 13/039170
DATED            : June 18, 2013
INVENTOR(S)      : D. James Morre It is certified that error appears in the above-identified patent and that said Letters Patent is hereby corrected as shown below:

ASSIGNEE

| Title Page | Kind Code | PTO | Should Read |
|---|---|---|---|
| 1 | (73) | "Nox Technologies, Inc., west Lafayette, IN" | -- Nox Technologies, Inc., West Lafayette, IN -- |

SPECIFICATION

| Column | Line | PTO | Should Read |
|---|---|---|---|
| 13 | 54-55 | "solubilized dilapidated apoB was" | -- solubilized delipidated apoB was -- |

Signed and Sealed this
Third Day of September, 2013

Teresa Stanek Rea
*Acting Director of the United States Patent and Trademark Office*